US012691412B2

(12) United States Patent
Alghamdi et al.

(10) Patent No.: US 12,691,412 B2
(45) Date of Patent: Jul. 28, 2026

(54) SYSTEMS AND METHODS FOR CAPTURING GREENHOUSE GASES UTILIZING ALGAE

(71) Applicant: Saudi Arabian Oil Company, Dhahran (SA)

(72) Inventors: Bassam M. Alghamdi, Dammam (SA); Musab M. Alqahtani, Dammam (SA); Norah A. Alkhathlan, Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 18/779,923

(22) Filed: Jul. 22, 2024

(65) Prior Publication Data

US 2026/0021448 A1 Jan. 22, 2026

(51) Int. Cl.
*B01D 53/84* (2006.01)
*B01D 53/34* (2006.01)
(Continued)

(52) U.S. Cl.
CPC ........... *B01D 53/84* (2013.01); *B01D 53/346* (2013.01); *B01D 53/92* (2013.01); *C12M 43/04* (2013.01); *B01D 2257/504* (2013.01); *B01D 2258/01* (2013.01); *C12M 1/002* (2013.01); *C12M 1/36* (2013.01); *C12M 21/02* (2013.01); *C12M 41/48* (2013.01)

(58) Field of Classification Search
USPC .................................................... 435/292.1
See application file for complete search history.

(56) References Cited

U.S. PATENT DOCUMENTS

2010/0255458 A1* 10/2010 Kinkaid ................... C12N 1/20
435/257.1
2017/0107478 A1* 4/2017 Harmon ................. C12M 23/44
(Continued)

FOREIGN PATENT DOCUMENTS

WO WO-2025227221 A1 * 11/2025 ............... C12N 1/12

OTHER PUBLICATIONS

Teague. "Machine Learning for Flow Cytometry" https://cytoflow.readthedocs.io/en/1.2/dev_manual/tutorials/machine_learning.html (Year: 2022).*

(Continued)

*Primary Examiner* — Michael A Marcheschi
*Assistant Examiner* — Nathan G Esperon
(74) *Attorney, Agent, or Firm* — Dinsmore & Shohl LLP

(57) ABSTRACT

A process for capturing greenhouse gas emissions utilizing algae may comprise feeding a carbon dioxide feed stream, a recycle water stream, and light to a closed photobioreactor, thereby forming oxygen and the algae; extracting the oxygen and at least a portion of the algae from the closed photobioreactor, the algae extracted as a wet biomass stream; introducing the wet biomass stream to a dewatering unit along with an exhaust gas stream comprising carbon dioxide, thereby forming steam, a reduced temperature exhaust gas stream, and a dehydrated biomass product; introducing at least a portion of the steam to a cooling unit, thereby condensing the steam and forming the recycle water stream; and introducing the reduced temperature exhaust gas stream to a treatment unit, thereby forming the carbon dioxide feed stream.

6 Claims, 5 Drawing Sheets

(51) Int. Cl.

| | | |
|---|---|---|
| B01D 53/92 | (2006.01) | |
| C12M 1/00 | (2006.01) | |
| C12M 1/36 | (2006.01) | |

(56) References Cited

U.S. PATENT DOCUMENTS

| | | | | |
|---|---|---|---|---|
| 2020/0066369 | A1* | 2/2020 | Downey | C12N 5/0602 |
| 2020/0199506 | A1* | 6/2020 | Flynn | C12M 23/20 |
| 2022/0259535 | A1* | 8/2022 | Kim | C12M 41/00 |
| 2024/0304284 | A1* | 9/2024 | McCready | G16B 40/20 |
| 2025/0230388 | A1* | 7/2025 | Clary | C12M 21/02 |

OTHER PUBLICATIONS

Moreira et al., "Atmospheric CO2 capture by algae: Negative carbon dioxide emission path", Bioresource Technology, vol. 215, pp. 371-379, Sep. 2016.
Paul et al., "Review on the recent structural advances in open and closed systems for carbon capture through algae", Energy Nexus, vol. 4, 100032, pp. 1-16, 2021.
Shekh et al., "Microalgae Cultivation: Photobioreactors, CO2 Utilization, and Value-Added Products of Industrial Importance", Manuscript, 2022.
Tripathi et al., "Carbon capture, storage, and usage with microalgae: a review", Environmental Chemistry Letters, vol. 21, pp. 2085-2128, 2023.
Wilson et al., "CO2 recycling using microalgae for the production of fuels", Appl Petrochem Res, vol. 4, pp. 41-53, 2014.

* cited by examiner

SYSTEMS AND METHODS FOR CAPTURING GREENHOUSE GASES UTILIZING ALGAE

FIELD

The present disclosure generally relates to the capture of greenhouse gases, and more particularly, to methods for capturing greenhouse gases such as carbon dioxide utilizing algae, as detailed herein. Additionally, embodiments herein relate to systems and methods for the optimization of algae life cycles utilizing a machine learning algorithm.

BACKGROUND

In the chemical industry, decarbonization technologies are continually being developed due to carbon dioxide ($CO_2$) emissions being a source of global climate change. Particularly, a number of industries and entities have devoted themselves to net-zero carbon dioxide emission initiatives. Nonetheless, fossil fuels remain the predominant energy source worldwide, such as in the form of natural gas for driving combustion gas turbines. Accordingly, carbon dioxide emissions remain a concern.

SUMMARY

Accordingly, methods are desired by which carbon dioxide, and particularly exhaust gases from fossil fuels, can be captured and utilized for positive applications. Embodiments herein address the aforementioned need by providing systems and processes for capturing greenhouse gases utilizing algae grown from water, carbon dioxide, and light in a closed photobioreactor, producing primarily oxygen and wet biomass as products. The biomass, when dehydrated, may then be subsequently used as a biofuel, food product, or fertilizer, as appropriate.

However, carbon capture utilizing algae may not be as simple as adding water, carbon dioxide, nutrients, and light and letting algae grow. Particularly, algae growth rates and life cycles may vary depending on a number of variables, including nutrient content, temperature, pH, light intensity, carbon dioxide content, oxygen content, and contaminant content. Too low of nutrient content, carbon dioxide content, or light intensity may starve algae for growth. Conversely, too high of carbon dioxide content may result of excess amount of carbonic acid, decreasing the pH of the photobioreactor and reducing enzyme activity, thereby slowing algae growth. Similarly, too high of temperature or light intensity may kill the algae bacteria/enzymes or induce photoinhibition.

Accordingly, to address these concerns, an exhaust gas stream, such as hot exhaust gas from a combustion gas turbine, and a wet biomass stream from a closed photobioreactor may be fed to a dewatering unit. The hot exhaust gas stream may operate to dewater the wet biomass stream by vaporizing water in the wet biomass stream and forming steam, whereas the wet biomass stream conversely cools down the hot exhaust gas stream. The reduction of temperature in the hot exhaust stream may operate to prevent algae loss in the photobioreactor when the exhaust gas is subsequently fed there as a carbon dioxide feed stream. Finally, the formed steam from the wet biomass stream may be subsequently cooled by exposure to a cooling unit, such as a refrigerator, to account for the temperature gain by exposure to the exhaust gas stream.

Moreover, a controller may be configured to optimize a life cycle of the algae in the closed photobioreactor by conducting a machine learning algorithm, thereby determining optimal amounts of various algae growth variables, as well as accounting for compositional and temperature changes in the exhaust gas steam by the introduction of oxygen or air into the carbon dioxide stream as well as varying of the cooling loop.

In accordance with one embodiment of the present disclosure, a process for capturing greenhouse gas emissions utilizing algae may comprise feeding a carbon dioxide feed stream, a recycle water stream, and light to a closed photobioreactor, thereby forming oxygen and the algae; extracting the oxygen and at least a portion of the algae from the closed photobioreactor, the algae extracted as a wet biomass stream; introducing the wet biomass stream to a dewatering unit along with an exhaust gas stream comprising carbon dioxide, thereby forming steam, a reduced temperature exhaust gas stream, and a dehydrated biomass product; introducing at least a portion of the steam to a cooling unit, thereby condensing the steam and forming the recycle water stream; and introducing the reduced temperature exhaust gas stream to a treatment unit, thereby forming the carbon dioxide feed stream.

In accordance with another embodiment of the present disclosure, a system for capturing greenhouse gas emissions utilizing algae may comprise a source of exhaust gas comprising carbon dioxide; a closed photobioreactor configured to receive a carbon dioxide feed stream and a recycle water stream and to generate the algae and oxygen; a light source configured to expose at least a portion of the photobioreactor to light; a dewatering unit fluidly connected downstream from the source of exhaust gas and the closed photobioreactor, wherein the dewatering unit is configured to dewater a wet biomass stream and an exhaust gas stream to form steam, a dehydrated biomass stream, and a reduced temperature exhaust gas stream; a treatment unit fluidly connected downstream from the dewatering unit and configured to remove one or more contaminants from the reduced temperature exhaust gas stream and form the carbon dioxide feed stream; and a cooling unit fluidly connected downstream from the dewatering unit and configured to cool the steam to form the recycle water stream.

BRIEF DESCRIPTION OF THE DRAWINGS

The following detailed description of specific embodiments of the present disclosure can be best understood when read in conjunction with the following drawings, where like structure is indicated with like reference numerals and in which.

Figure 1:
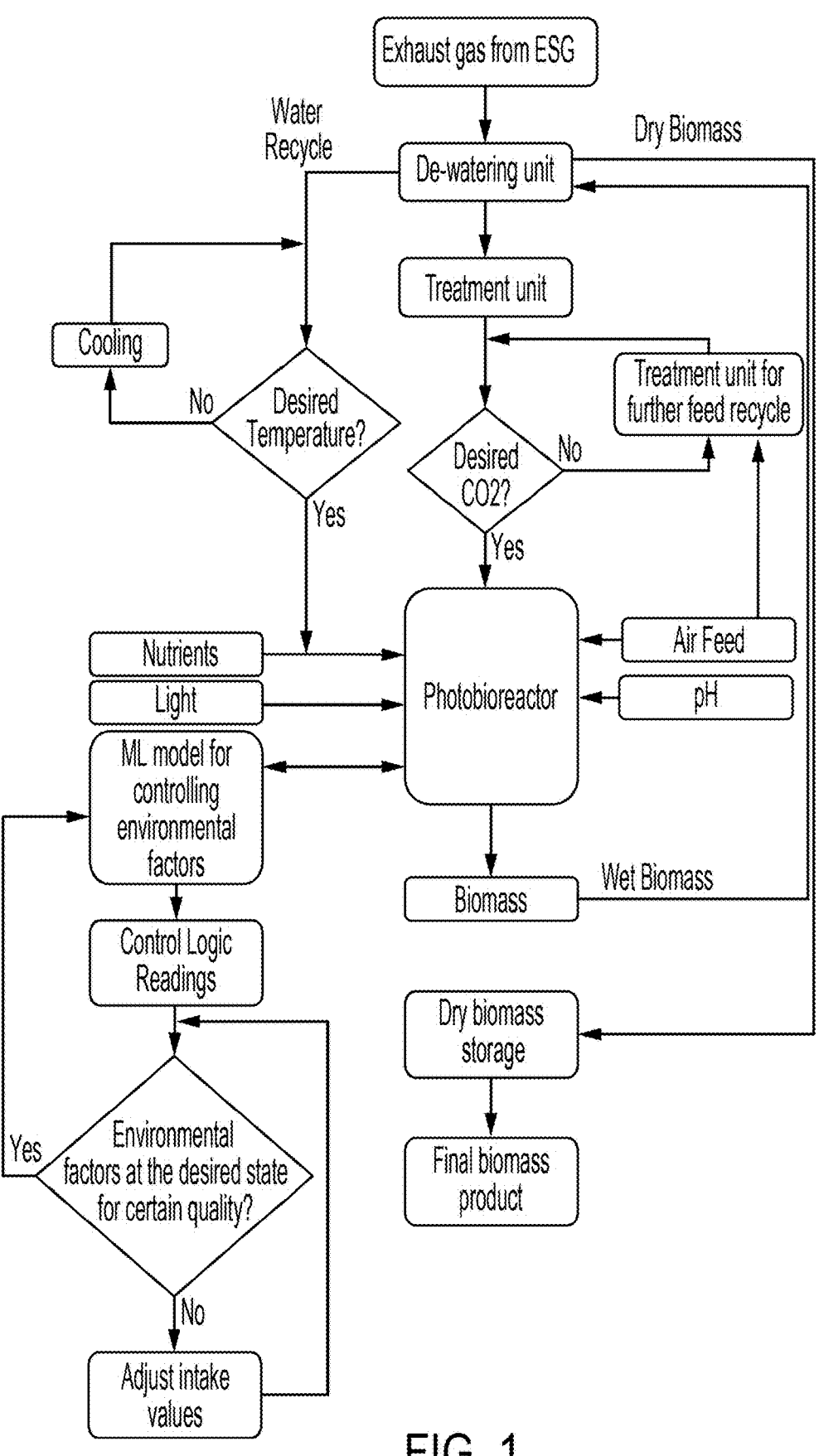
FIG. 1 illustrates a process diagram for capturing greenhouse gas emissions utilizing algae, according to one or more embodiments herein.

With reference to the figures, the following is intended to act as a legend for the purposes of the many abbreviations contained in the examples. "FT" and "FI" refer to a flow transmitter and a flow indicator respectively. "TT", "TI", "TCV" refer to a temperature transmitter, a temperature indicator, and a temperature control valve respectively. "PT", "PI", and "PCV" refer to a pressure transmitter, a pressure indicator, and a pressure control valve respectively. "ML" refers to machine learning. "FC", "FTD", and "FCV" refer to a flow controller, flow transducer, and a flow control valve respectively. "LIS" refers to a light intensity sensor. "AIT", "QA", "AE", and "AI" refer to an analyzer indication transmitter, a quality analyzer, an analyzer element, and an analyzer indictor respectively. "EGS" refers to an exhaust gas source, which may be a heat recovery steam generator (HRSG), as described in more detail herein.

Further, with reference to the figures, the following is intended to act as a legend for some of the symbols used in the figures. The symbol $\bigcirc$ is intended to represent an indicator, i.e. a sensor. The sensor may also include a transmitter for transmitting the information collected by the sensor, which may or may not be illustrated in the figures.

The symbol $\boxed{MCL}$ is intended to represent a controller, with the various controllers illustrated referring to the same controller responsible for executing the machine learning algorithm (also designated "master control logic"), or a plurality of microcontrollers reporting to the controller responsible for executing the machine learning algorithm. The symbols $\boxtimes$ and $\boxtimes$ are intended to illustrate as control valve along with an associated actuator. The symbol $\boxed{}$ is intended to represent a distributed control system (DCS) and in particular as a collective symbol to represent the one or more controllers, as well as the associated control valves and actuators. The symbol $\boxed{}$ is intended to represent a computer containing the processor and the one or more controllers/microprocessors for executing the machine learning algorithm.

For the purpose of describing the simplified schematic illustrations and descriptions of the relevant figures, some of the numerous valves, temperature sensors, electronic controllers and the like that may be employed and well known to those of ordinary skill in the art of certain chemical processing operations may not always be included. It should be understood that these components, where not included, are still within the spirit and scope of the present embodiments disclosed. However, operational components, such as those described in the present disclosure, may be added to the embodiments described in this disclosure.

It should further be noted that arrows with solid lines in the drawings refer to process streams. However, the arrows may equivalently refer to transfer lines, which may serve to transfer process streams between two or more system components. Additionally, arrows that connect to system components define inlets or outlets in each given system component. The arrow direction corresponds generally with the major direction of movement of the materials of the stream contained within the physical transfer line signified by the arrow. Furthermore, arrows, which do not connect two or more system components, signify a product stream, which exits the depicted system, or a system inlet stream, which enters the depicted system. Product streams may be further processed in accompanying chemical processing systems or may be commercialized as end products. System inlet streams may be streams transferred from accompanying chemical processing systems or may be non-processed feedstock streams. Some arrows may represent recycle streams, which are effluent streams of system components that are recycled back into the system. However, it should be understood that any represented recycle stream, in some embodiments, may be replaced by a system inlet stream of the same material, and that a portion of a recycle stream may exit the system as a product. Further, it should be noted that any solid lines in the drawings having two front slashes "$\#$", refer to an instrument air or hydraulic line, such as that to supply force to an actuator to actuate one or more of the control valves in the system described herein.

Similarly, it should be further noted that arrows with dashed lines in the drawings refer to electronic communication links between two or more components, which may be wireless or wired. Solid lines interposed with open circles may depict a subset of electronic communication links, such as a "soft signal" between two or more components.

Additionally, arrows in the drawings may schematically depict process steps of transporting a stream from one system component to another system component. For example, an arrow from one system component pointing to another system component may represent "passing" a system component effluent to another system component, which may include the contents of a process stream "exiting" or being "removed" from one system component and "introducing" the contents of that product stream to another system component.

It should be understood that according to the embodiments presented in the relevant figures, an arrow between two system components may signify that the stream is not processed between the two system components. In other embodiments, the stream signified by the arrow may have substantially the same composition throughout its transport between the two system components. Additionally, it should be understood that in embodiments, an arrow may represent that at least 75 wt. %, at least 90 wt. %, at least 95 wt. %, at least 99 wt. %, at least 99.9 wt. %, or even 100 wt. % of the stream is transported between the system components. As such, in embodiments, less than all of the stream signified by an arrow may be transported between the system components, such as if a slip stream is present.

It should be understood that two or more process streams are "mixed" or "combined" when two or more lines intersect in the schematic flow diagrams of the relevant figures. Mixing or combining may also include mixing by directly introducing both streams into a like reactor, separation unit, or other system component. For example, it should be understood that when two streams are depicted as being combined directly prior to entering a separation unit or reactor, that in embodiments the streams could equivalently be introduced into the separation unit or reactor and be mixed in the reactor. Alternatively, when two streams are depicted to independently enter a system component, they may in embodiments be mixed together before entering that system component.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

As previously stated, embodiments described herein generally relate to the capture of greenhouse gases, and more particularly, to methods for capturing greenhouse gases such as carbon dioxide utilizing algae, as detailed herein. Additionally, embodiments herein relate to systems and methods for the optimization of algae life cycles utilizing a machine learning algorithm.

Figure 2:
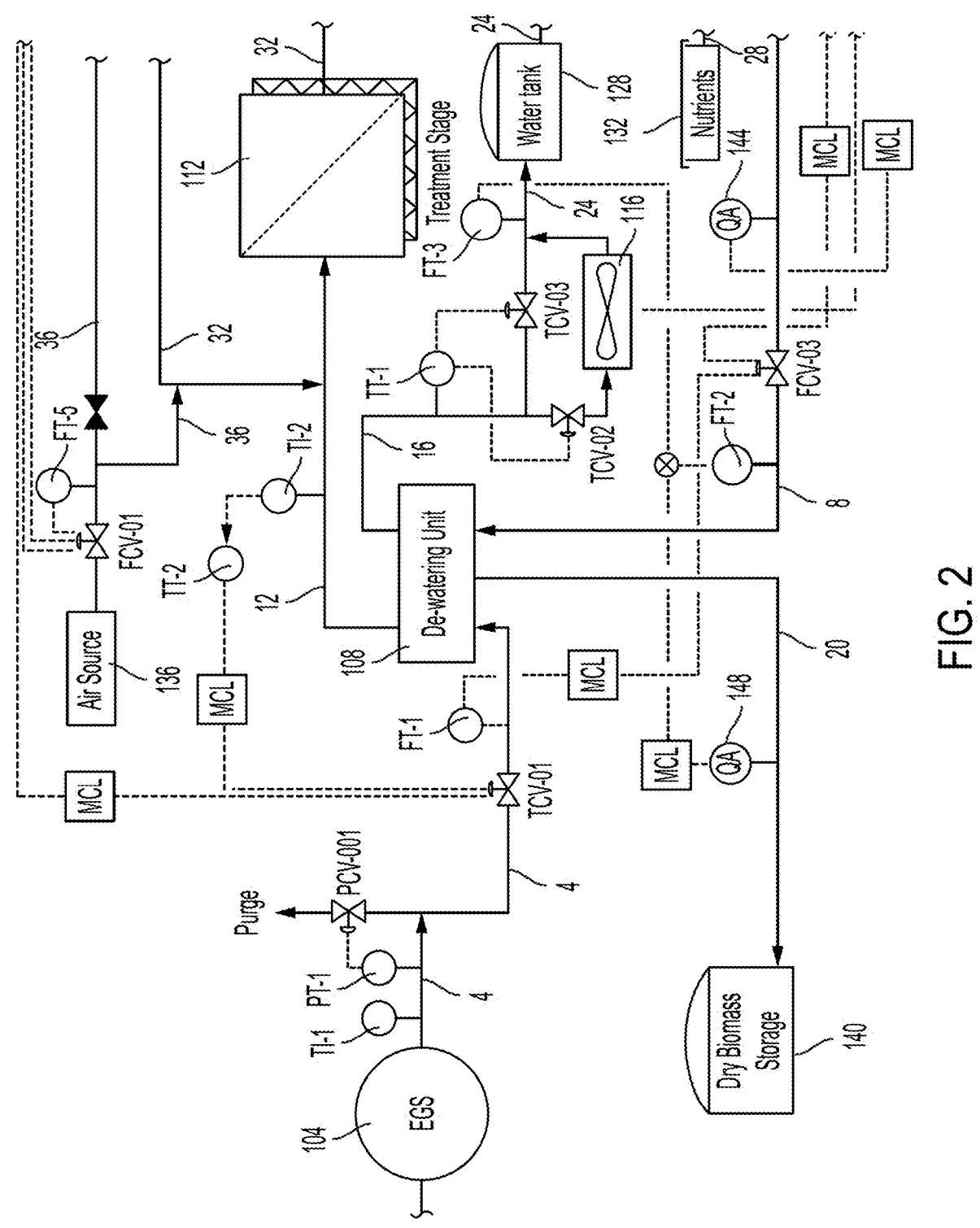
FIG. 2 illustrates a system for capturing greenhouse gas emission utilizing algae according to one or more embodiments herein.
Figure 2:
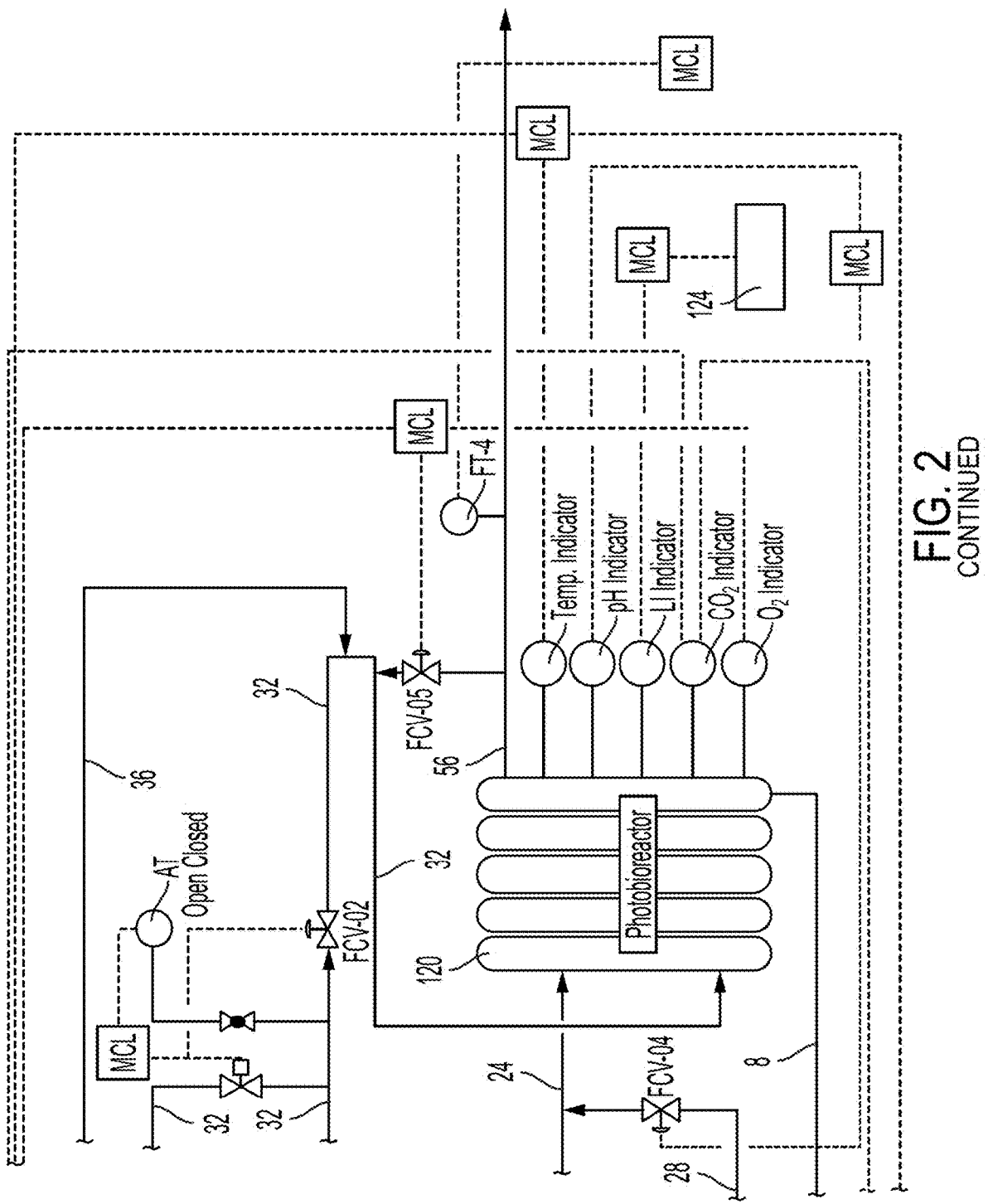

Referring initially to FIGS. 1 and 2, illustrated is a system 100 for capturing greenhouse gas emissions utilizing algae. As shown in FIGS. 1 and 2, the system 100 may comprise a exhaust gas source 104, a dewatering unit 108 fluidly connected downstream of the exhaust gas source 104, a treatment unit 112 fluidly connected downstream of the dewatering unit 108, a cooling unit 116 fluidly connected downstream of the dewatering unit 108, a closed photobioreactor 120 fluidly connected downstream of the treatment unit 112 and fluidly connected upstream of the dewatering unit 108, and a light source 124 configured to supply light to at least a portion of the closed photobioreactor 120. As shown in FIGS. 1 and 2, the system 100 may comprise a variety of flow lines within which control valves may be positioned to redirect streams from one flow line to another, or to open closed bypass lines or recycle lines to flow, as may be understood in the art. Furthermore, the system 100 may comprise a plurality of sensors for sensing one or more properties of the fluids of the system 100, as may be understood in the art. Where appropriate, these sensors, bypass lines, and recycle lines are name and/or labeled to designate the general category of measurement and/or flow.

As previously stated, the system 100 may be utilized to generate algae. In embodiments, the algae may include, but may not be limited to, genera such as *Chlorella, Arthrospira*, or species thereof, such as *Arthrospira (Spirulina) platensis* or *Chlorella* sp. However, it is contemplated that the present systems may be utilized or adapted for any genus of algae utilizing the machine learning algorithm and optimizing one or more of the algae growth variables.

As previously stated, the system 100 may comprise the exhaust gas source 104. The exhaust gas source 104 may comprise a combustion device configured to generate an exhaust gas stream 4 comprising carbon dioxide as a byproduct of the combustion coming from such as, but not limited to, a combustion gas turbine. In embodiments, the exhaust gas source 104 may be configured to send the exhaust gas stream 4 to the dewatering unit 108. Without being limited by theory, the exhaust gas stream 4 may have an elevated temperature owing to the combustion process. Accordingly, as explained in further detail herein, it may be desired to cool the exhaust gas stream 4 prior to feeding into the photobioreactor to avoid reducing the life cycle of the algae in the same. In embodiments, the exhaust gas stream 4 may have a temperature of from 150° C. to 200° C.

As previously stated, the system 100 may comprise the dewatering unit 108, which may be fluidly connected downstream of the exhaust gas source 104 and the closed photobioreactor 120 such as through one or more flow lines. The dewatering unit 108 may also be configured to receive the exhaust gas stream 4 from the exhaust gas source 104 and a wet biomass stream 8 from the closed photobioreactor 120. For example, and in embodiments, as the algae in the closed photobioreactor 120 reaches the end of its lifecycle, it may die and form biomass, which may be extracted as the wet biomass stream 8. The dewatering unit 108 may be configured to thermally expose the wet biomass stream 8 to the exhaust gas stream 4 (i.e. through a heat exchanger), resulting in a temperature exchange between the streams and separately forming a reduced temperature exhaust gas stream 12 as well as steam 16 and dehydrated biomass 20. In at least some embodiments, the dewatering unit 108 may further be configured to dewater at least the wet biomass stream 8 via thermal heat exchange and evaporation, such as through a heat recovery steam 16 generator (HRSG). Without being limited by theory, thermally exposing the relatively lower temperature wet biomass to the relatively higher exhaust gas stream 4 and producing the steam 16 may be advantageous to reduce undesired bacterial content in the recycle water stream 24 that may be recycled to the closed photobioreactor 120, as explained in further detail herein.

Still referring to FIGS. 1 and 2, the system 100 may comprise the cooling unit 116, which may fluidly connected downstream from the dewatering unit 108 and fluidly connected upstream from the closed photobioreactor 120, such as through one or more flow lines. The cooling unit 116 may be configured to receive at least a portion of the steam 16 from the dewatering unit 108 and cool and/or condense the same, thereby forming the recycle water stream 24. The cooling unit 116 may also be configured to send the recycle water stream 24 to the closed photobioreactor 120. In embodiments, the cooling unit 116 may comprise a refrigeration unit, fin or fan coolers, cooling towers, or combinations thereof. In embodiments, the provision of the cooling unit 116 may enable the cooling of the recycle water stream 24 back to a temperature at which the recycle water stream 24 will not negatively impact the algae life cycle when reintroduced to the closed photobioreactor 120. As also shown in FIGS. 1 and 2, and in at least some embodiments, the system 100 may further comprise a water tank 128. The water tank 128 may be interposed between the cooler and the closed photobioreactor 120, the water tank 128 and the closed photobioreactor 120, or both, for storage and cooling of the steam 16 and/or recycled water stream before recycling to the closed photobioreactor 120, as appropriate.

Without being limited by theory, it may be necessary to periodically resupply the closed photobioreactor 120 with nutrients to replace those lost with extraction of the wet biomass stream 8. Accordingly, and still referring to FIGS. 1 and 2, the system 100 may further comprise a nutrient tank 132 fluidly connected upstream of the photobioreactor, such as through one or more flow lines which may be connected to those flow lines connecting the cooler and the closed photobioreactor 120. The nutrient tank 132 may be configured to send a nutrient stream 28 comprising one of a number of algae growth nutrients to the photobioreactor, including but not limited to compounds containing nitrogen, phosphorous, potassium, calcium, magnesium, sulfur, or combinations thereof. For example, the nutrient stream 28 may comprise nitrates and phosphates. However, the algae growth nutrients may also comprise compounds of boron, copper, iron, manganese, zinc, chlorine, cobalt, or combinations thereof. In embodiments, and as shown in FIGS. 1 and 2, the nutrient tank 132 may also be configured to provide the nutrient stream 28 to the recycle water stream 24 prior to feeding into the closed photobioreactor 120.

As previously stated, the dewatering unit 108 may be configured to form the reduced temperature exhaust gas stream 12 from the exhaust gas stream 4, which may also comprise carbon dioxide for feeding to the closed photobioreactor 120. However, due at least to the potential presence of contaminants in the exhaust gas stream 4, such as carbon monoxide, nitrogen monoxide, nitrogen dioxide, sulfur oxides, and ammonia, it may be desired to further treat the reduced temperature exhaust gas stream 12 prior to feeding to the closed photobioreactor 120. Without being limited by theory, the amount and/or type of contaminants in the exhaust gas stream 4 may be dependent on the source of exhaust gas used.

Accordingly, as shown in FIGS. 1 and 2, and as previously stated, the system 100 may further comprise the treatment unit 112 fluidly connected downstream of the dewatering unit 108 such as through one or more flow lines. The treatment unit 112 may receive the reduced temperature exhaust gas stream 12 and treat the same to produce a carbon dioxide feed stream 32. The treatment unit 112 may comprise one or more absorption columns, oxidation columns, membrane separation columns, or combinations thereof for removing the contaminants from the reduced temperature exhaust gas stream 12. As shown in FIGS. 1 and 2, the treatment unit 112 may also be fluidly connected upstream of the photobioreactor through one or more flow lines such that the treatment unit 112 may feed the carbon dioxide feed stream 32 to the closed photobioreactor 120.

As explained in further detail herein, carbon dioxide content in the closed photobioreactor 120 may be an important factor in algae growth and life cycle enhancement, as excess levels of carbon dioxide may result in acidification of the closed photobioreactor 120 and death of algae species. Accordingly, when carbon dioxide content is too high in the closed photobioreactor 120, it may be desired to decrease the carbon dioxide content of the carbon dioxide feed stream 32. Accordingly, the system 100 may further comprise an external source of air 136 comprising air 36. As shown in FIGS. 1 and 2, the external source of air 136 may be fluidly connected upstream of the treatment unit 112, the closed photobioreactor 120, or both, and may particularly be fluidly connected to the lines for transferring the reduced temperature exhaust gas stream 12, the carbon dioxide feed stream 32 or both. Accordingly, the external source of air 136, such as through one or more control valves, may be configured to introduce the air 136 to the reduced temperature exhaust gas stream 12, the carbon dioxide feed stream 32 or both for reducing a carbon dioxide content in the former and the latter.

Additionally or alternatively, the closed photobioreactor 120 may comprise one or more recycle lines for recycling the oxygen produced from the closed photobioreactor 120 to the carbon dioxide feed stream 32 as an oxygen recycle stream 56, thereby reducing the carbon dioxide content in the same. Flow through the recycle lines may be controlled through one or more control valves, as shown in FIGS. 1 and 2.

Additionally or alternatively, it may be determined that the closed photobioreactor 120 does not comprise adequate carbon dioxide content for algae growth and lifecycle. Accordingly, the system 100 in at least one embodiment may comprise one or more recycle lines for recycling the carbon dioxide feed stream 32 to the treatment unit 112, for further treatment of the same and ideally further refinement of the stream to increase the carbon dioxide content. In a similar manner, it may be determined that the carbon dioxide feed stream 32 still contains an undesired level of contaminants. In such embodiments, the carbon dioxide feed stream 32 may also be recycled through the one or more recycle lines for further treatment, and ideally further refinement of the carbon dioxide feed stream 32 to decrease the contaminant content.

As previously stated, the dewatering unit 108 may be configured to form the dehydrated biomass product 20 from the wet biomass stream 8. As further shown in FIGS. 1 and 2, the dewatering unit 108 may be configured to send the dry biomass to a dry biomass storage vessel 140 connected downstream of the dewatering unit 108 for storing the dehydrated biomass product 20, such as through one or more flow lines or through a conveyer system 100, as may be understood in the art. While not illustrated, there may also be one or more dehydrated biomass 20 refining units interposed between the dewatering unit 108 and the dry biomass storage vessel 140, or alternatively as a part of the dry biomass storage vessel 140 for further treatment of the dehydrate biomass product. For example, and in embodiments, the one or more dehydrated biomass 20 refining units may comprise a pelletizer unit, a briquette unit, a supplemental dryer, or combinations thereof.

Still referring to FIGS. 1 and 2, and as previously stated, the system 100 may comprise the closed photobioreactor 120. The closed photobioreactor 120 may be configured to receive at least the carbon dioxide feed stream 32 and the recycle water feed stream for forming the oxygen and the algae. As previously stated, the growth and lifecycle of the algae may be dependent on a plurality of factors, referred to herein as algae growth variables, including the carbon dioxide content, the pH (which in turn may be co-dependent on the carbon dioxide content), the oxygen content, the contaminant content, the nutrient content, the temperature, and the light quality. Accordingly, as previously stated, the system 100 may further comprise the light source 124 for exposing the closed photobioreactor 120 to light. Without being limited by theory, the light quality may in turn be dependent on the placement of the light source 124 with respect to the photobioreactor (as well as where it is not placed, i.e., the dark zones on the photobioreactor) as well as the light intensity. Particularly, algae growth may be impacted by the intensity of the light source 124, as too severe a light may induce photoinhibition, negatively impacting algae growth.

As previously stated, the growth and lifecycle of the algae in the closed photobioreactor 120 may be dependent on the plurality of algae growth variables. Accordingly, to monitor these variables, the system 100 may further comprise a plurality of sensors coupled to the closed photobioreactor 120 that are configured to monitor the plurality of algae growth variables. The plurality of sensors may comprise a gas chromatograph, a pH sensor, a photosensitive sensor, a temperature sensor, and a nutrient quality analyzer for measuring the carbon dioxide content, the pH, the light intensity, the temperature, and the nutrient content respectively. The gas chromatograph may also be configured to measure oxygen content and contaminant content as may be required. In embodiments, the nutrient quality analyzer may take into account data obtained from the pH sensor and the biomass quality analyzers (as described below) to generate an indicator of whether the closed photobioreactor 120 contains sufficient nutrients.

As shown in FIGS. 1 and 2, the plurality of sensors may comprise additional sensors other than those coupled to the closed photobioreactor 120. For example, and as shown in FIGS. 1 and 2, the system 100 may further comprise a wet biomass quality analyzer 144 configure to analyze a content of the wet biomass stream 8, a dry biomass quality analyzer 148 configured to analyze a content of the dry biomass product, as well as a sensor configured to analyze an oxygen content extracted from the closed photobioreactor 120, which may be a gas chromatograph as previously discussed.

It is contemplated that the quality analyzers may determine a moisture content, an oxygen content, a density, a weight, and a chlorophyll content of the biomass streams. The quality analyzers may in turn incorporate a Near-Infrared Spectroscopy sensor (NIR), an Optical Density sensor, an Element Analyzer, or combinations thereof to measure these qualities.

As previously stated, embodiments herein also relate to systems and methods for the optimization of algae life cycles utilizing a machine learning algorithm. Accordingly, as shown in FIGS. 1 and 2, the system 100 may further comprise a controller for controlling the one or more control valves and components in the system 100 in coordination with the plurality of sensors and the machine learning algorithm. Particularly, the controller may be programmed to execute the machine learning algorithm on the other components of the system 100 to optimize a life cycle of the algae in the closed photobioreactor 120. The controller may be communicatively coupled to the plurality of sensors and each of the plurality of control valves in the system 100, such as through actuators coupled to each of the plurality of control valves in the system 100. As previously stated, the controller(s) may be designated in the drawings by the symbol [MCL] .

For direct communication, it is contemplated that the plurality of sensors and the actuators coupled to the plurality of control valves, as well as at least the dewatering unit 108, light source 124, treatment unit 112, and cooler, may comprise a two-way data communications link connecting communications hardware of the previous to communications hardware of the controller. The controller may comprise a microcontroller unit, or it may comprise multiple or sub-microcontroller units. The microcontroller unit may comprise a processor communicatively coupled to a memory. The communications hardware of the microcontroller unit may receive data, such as the plurality of algae growth variables, from the plurality of sensors and transfer the data to be stored in the memory. The processor may be configured to pull the data from the memory, conduct one or more operations on the data according to the machine learning algorithm, which may also be stored on the memory, before communicating instructions to at least some of the actuators coupled to each of the plurality of control valves in the system 100, or to the one or more units of the system 100, such as to the dewatering unit 108, light source 124, treatment unit 112, and cooler.

As previously stated, the processor may be configured to conduct the machine learning algorithm. The algorithm may comprise monitoring the plurality of algae growth variables; and concurrently monitoring a lifecycle of the algae via the content of the oxygen and the wet biomass stream 8 extracted from the closed photobioreactor 120.

The algorithm may further comprise determining sensitivities between the lifecycle of the algae and the one or more algae growth variables by varying the plurality of algae growth variables, such as by altering the flow of the streams feeding the photobioreactor through the plurality of control valves (and thereby altering the $CO_2$ content, pH, oxygen content, contaminant content, or nutrient content as appropriate), a temperature of the photobioreactor through the cooling unit 116, and a light intensity by altering the light source 124. This may be regarded as a clustering portion of the algorithm, and may be used to develop the capacity of the subsequent algorithm to identify deviations from normal operating conditions based on the algae growth variables.

The algorithm may then comprise conducting machine learning on the sensitivities to determine an optimized level of one or more of the $CO_2$ content, the pH, the light intensity, the temperature, the oxygen content, or the nutrient content associated with an optimized and controlled lifecycle of the algae. This may be regarded as a classification portion of the algorithm, and may be used to develop the capacity of the algorithm to predict and determine the optimized and controlled lifecycle of the algae.

Figure 3:
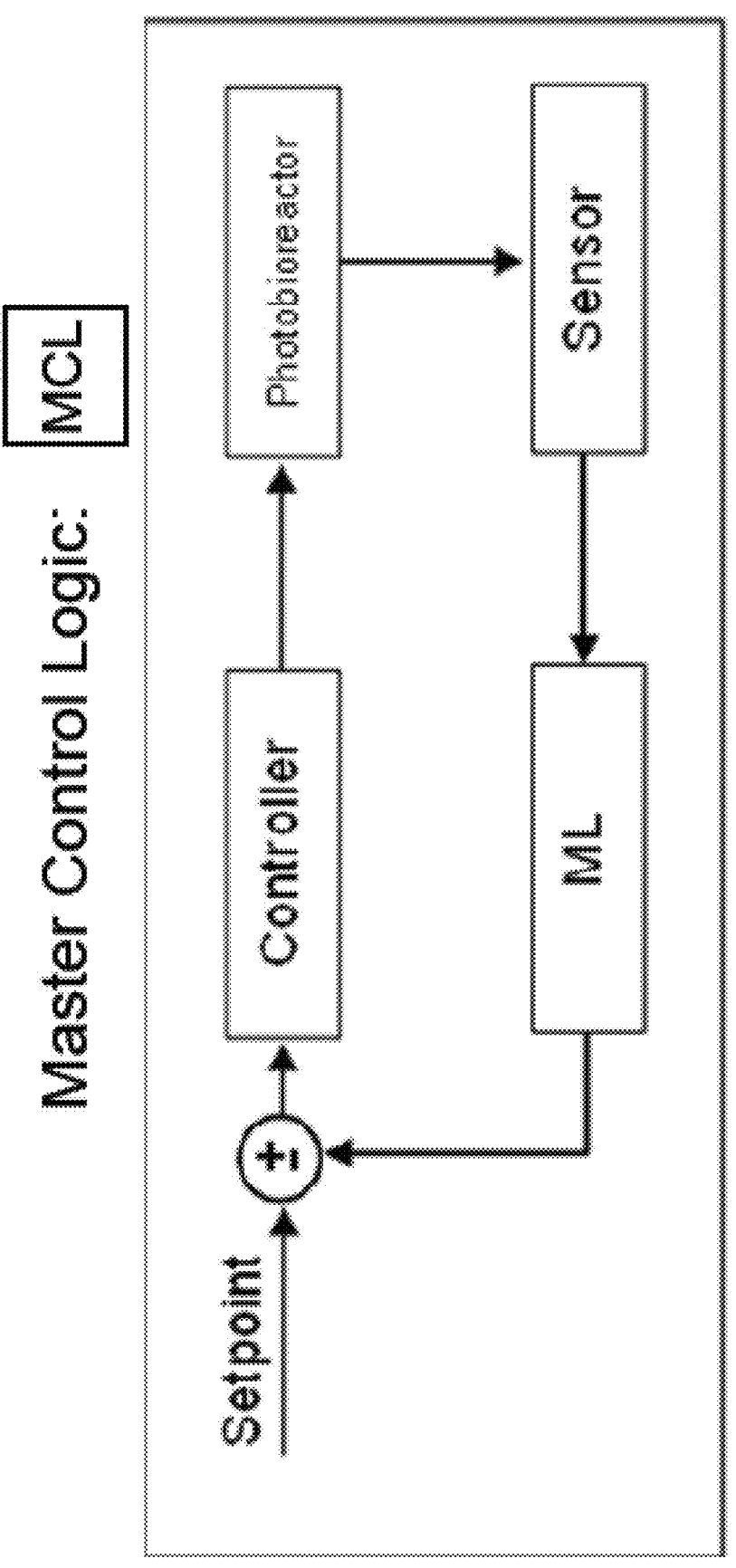
FIG. 3 illustrates a sample control loop for the machine learning algorithm/master control logic as it controls and optimizes one or more input parameters of the system, according to one or more embodiments herein.
Figure 4:
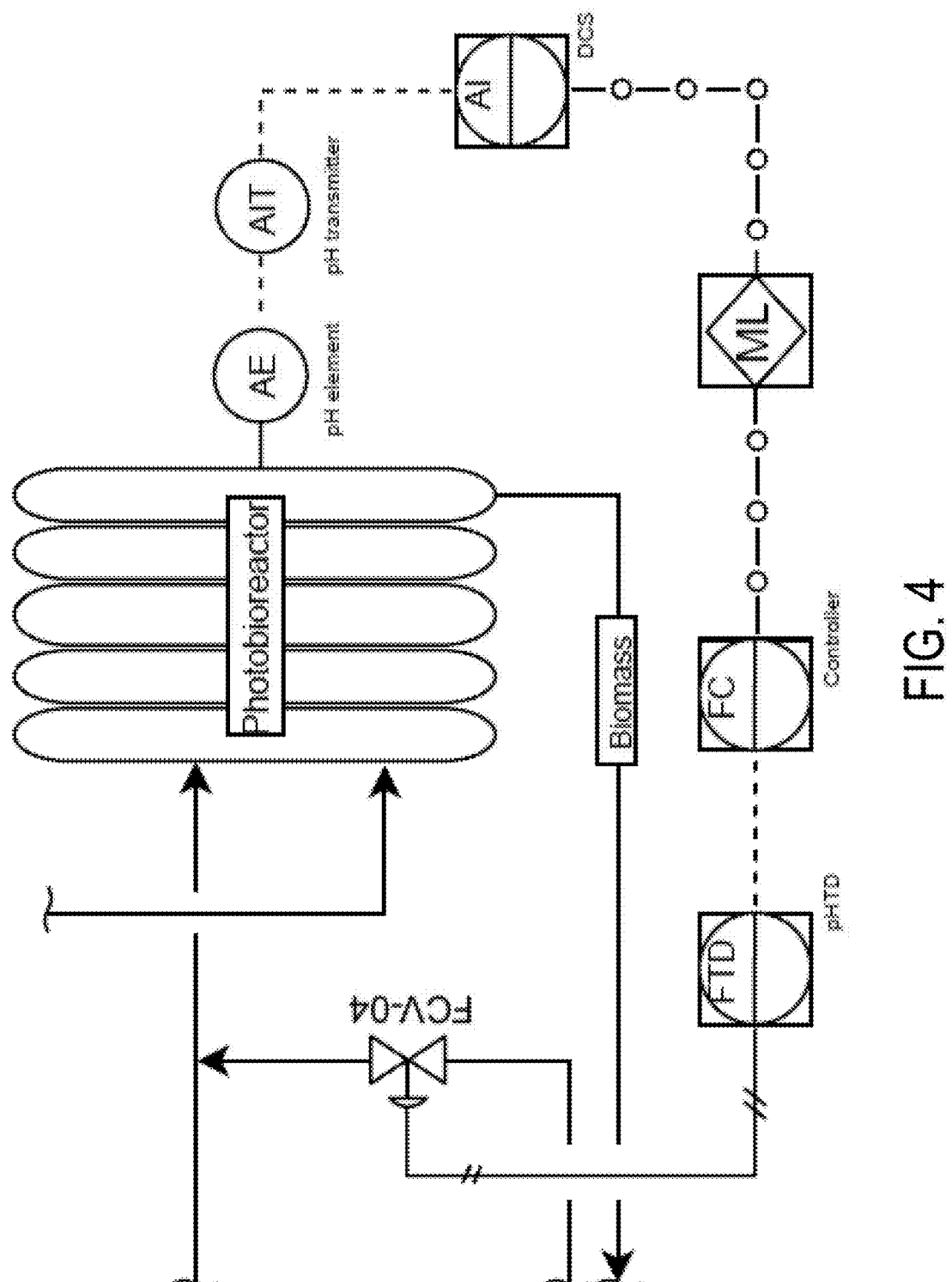
FIG. 4 illustrates a detailed sample control loop similar to FIG. 3 as applied to the system of FIG. 2, according one or more embodiment herein.

In embodiments, the controller may be configured to take one or more additional steps after conducting the machine learning algorithm. Particularly, the clustering and classification portions may be integrated with the system 100 for the closed photobioreactor 120, allowing the machine learning algorithm to learn and adjust to changes in the process dynamics, eventually optimizing the control system 100 parameters for improved performance. This is shown for example in FIGS. 3 (generally) and 4 (specifically), illustrating control loops for the algorithm and system. As shown in FIGS. 3 and 4, an algae growth variable, i.e. setpoint, (pH in FIG. 4) may be monitored by one or more of the sensors (pH sensor in FIG. 4) in which the data is then transmitted to the controller responsible for the machine learning algorithm/master control logic. The controller then determines whether the variable (pH in FIG. 4) is outside a predetermined tolerance, and if so, generates a signal to adjust one or more of the control valves responsible for adjusting one of the input parameters (nutrients in FIG. 4) to the system.

Similarly, in another illustrative example, and in embodiments, the controller may further be configured to monitor the $CO_2$ content of the carbon dioxide feed stream 32 concurrently with the feeding of the carbon dioxide feed stream 32 to the closed photobioreactor 120. Further, upon determining that the $CO_2$ content of the carbon dioxide feed stream 32 has exceeded a predetermined tolerance from the optimized $CO_2$ content associated with the optimized and controlled lifecycle of the algae, the controller may vary an introduction rate of the external air 136 source, the carbon dioxide feed stream 32, or both. Alternatively or additionally, the controller may vary a recycling rate of the oxygen into the carbon dioxide feed stream 32. The controller may be operable to conduct the previous such as by opening or closing of at least some of the plurality of control valves in the system 100 or adjusting a flow rate of one or more of the stream therein.

Additionally or alternatively, the controller may further be configured to monitor the temperature of the recycle water stream 24 concurrently with the feeding of the recycle water stream 24 to the closed photobioreactor 120; and upon determining that the temperature of the recycle water stream 24 has exceeded a predetermined tolerance from the optimized temperature associated with the optimized and controlled lifecycle of the algae, vary: an introduction percentage of the steam 16 into the cooling unit 116, a cooling capacity of the cooling unit 116, or both.

As previously stated, embodiments herein are also directed to methods for capturing greenhouse gases such as carbon dioxide utilizing algae, as well as methods for the optimization of algae life cycles utilizing a machine learning algorithm. The method may utilize any of the systems or machine learning algorithms hereinbefore discussed.

The method may comprise introducing the wet biomass stream 8 to a dewatering unit 108 along with an exhaust gas stream 4 comprising carbon dioxide, thereby forming the steam 16, the reduced temperature exhaust gas stream 12, and the dehydrated biomass product 20. The method may also comprise introducing the reduced temperature exhaust gas stream 12 to the treatment unit 112, thereby forming the carbon dioxide feed stream 32; and introducing at least a portion of the steam 16 to the cooling unit 116, thereby condensing the steam 16 and forming the recycle water stream 24.

The method may also comprise feeding the carbon dioxide feed stream 32, the recycle water stream 24, and light to the closed photobioreactor 120, thereby forming oxygen and the algae; and extracting the oxygen and at least a portion of the algae from the closed photobioreactor 120 as the wet biomass stream 8.

The method in at least one embodiment may comprise mixing at least a portion of the oxygen stream with the carbon dioxide stream, thereby reducing the carbon dioxide content of the carbon dioxide stream. The method may also comprise converting the dehydrated biomass product 20 into a plurality of dried biomass pellets, briquettes, or both, such as by utilizing the one or more dehydrated biomass 20 refining units previously described. The method may also comprise introducing an external air 136 source into the dehydrated exhaust stream, the carbon dioxide feed stream 32, or both. The method may also comprise supplementing the closed photobioreactor 120 with the nutrient stream 28, such as from the nutrient tank 132. The nutrient stream 28 may also be mixed with the recycle water stream 24 prior to the recycle water stream 24 being introduced to the closed photobioreactor 120.

Additionally or alternatively, the method may further comprise recycling at least a portion of the carbon dioxide feed stream 32 back to the treatment unit 112 to further treat the said portion and reduce a level of contaminants in the carbon dioxide feed stream 32 fed to the closed photobioreactor 120.

As previously stated, the system 100 may further comprise the controller that may be configured to optimize the life cycle of the algae in the closed photobioreactor 120. Particularly, the controller may optimize the life cycle of the algae by conducting the machine learning algorithm. Accordingly, the method may further comprise, through the controller, monitoring the plurality of algae growth variables in the photobioreactor utilizing the plurality of sensors; concurrently monitoring the lifecycle of the algae via the content of the oxygen and the wet biomass stream 8 extracted from the closed photobioreactor 120; determining the sensitivities between the lifecycle of the algae and the one or more algae growth variables by varying the plurality of algae growth variables; and conducting machine learning on the sensitivities to determine the optimized level of one or more of the $CO_2$ content, the pH, the light intensity, the temperature, the oxygen content, or the nutrient content associated with an optimized and controlled lifecycle of the algae.

The method may also comprise monitoring the $CO_2$ content of the carbon dioxide feed stream 32 concurrently with the feeding of the carbon dioxide feed stream 32 to the closed photobioreactor 120; and upon determining that the $CO_2$ content of the carbon dioxide feed stream 32 has exceeded a predetermined tolerance from the optimized $CO_2$ content associated with the optimized and controlled lifecycle of the algae, varying: an introduction rate of an external air 136 source into the reduced temperature exhaust gas stream 12, the carbon dioxide feed stream 32, or both, a recycling rate of the oxygen into the carbon dioxide feed stream 32; or both.

The method may additionally or alternatively comprise monitoring the temperature of the recycle water stream 24 concurrently with the feeding of the recycle water stream 24 to the closed photobioreactor 120; and upon determining that the temperature of the recycle water stream 24 has exceeded a predetermined tolerance from the optimized temperature associated with the optimized and controlled lifecycle of the algae, varying: an introduction percentage of the steam 16 into the cooling unit 116, a cooling capacity of the cooling unit 116, or both.

In a general sense with reference to FIG. 3, the method may additionally or alternatively comprise monitoring one of the plurality of algae growth variables; and upon determining that the one of the plurality of algae growth variables has exceeded a predetermined tolerance from the optimized algae growth variable setpoint associated with the optimized and controlled lifecycle of the algae, varying the algae growth variable. For example, in the case of pH, altering an introduction rate of the recycle water stream 24, the carbon dioxide feed stream 32 and/or the nutrient stream 28 into the closed photobioreactor 120. In the case of oxygen content, varying a recycling rate of the oxygen into the carbon dioxide feed stream 32 or an introduction rate of an external air 136 source into the reduced temperature exhaust gas stream 12, the carbon dioxide feed stream 32, or both. In the case of nutrient content, varying an introduction rate of the nutrient stream 28 into the close photobioreactor 120. In the case of light intensity, varying a light intensity provided by the light source 124 to the closed photobioreactor 120.

For the purposes of describing and defining the present invention, it is noted that reference herein to a variable being a "function" of a parameter or another variable is not intended to denote that the variable is exclusively a function of the listed parameter or variable. Rather, reference herein to a variable that is a "function" of a listed parameter is intended to be open ended such that the variable may be a function of a single parameter or a plurality of parameters.

It is noted that recitations in the present disclosure of a component of the present disclosure being "operable" or "sufficient" in a particular way, to embody a particular property, or to function in a particular manner, are structural recitations, as opposed to recitations of intended use. More specifically, the references in the present disclosure to the manner in which a component is "operable" or "sufficient" denotes an existing physical condition of the component and, as such, is to be taken as a definite recitation of the structural characteristics of the component.

It is also noted that recitations herein of "at least one" component, element, etc., should not be used to create an inference that the alternative use of the articles "a" or "an" should be limited to a single component, element, etc. The singular forms "a," "an" and "the" include plural referents, unless the context clearly dictates otherwise.

Throughout this disclosure ranges are provided. It is envisioned that each discrete value encompassed by the ranges are also included. Additionally, the ranges which may be formed by each discrete value encompassed by the explicitly disclosed ranges are equally envisioned.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising." It is noted that the use of the terms "having" or "including", or grammatical variations thereof, in this disclosure should also be interpreted in like manner as the more commonly used open-ended preamble term "comprising".

It is noted that recitations herein of a component of the present disclosure being "configured" or "programmed" in a particular way, to embody a particular property, or to function in a particular manner, are structural recitations, as opposed to recitations of intended use. More specifically, the references herein to the manner in which a component is "configured" or "programmed" denotes an existing physical condition of the component and, as such, is to be taken as a definite recitation of the structural characteristics of the component.

Having described the subject matter of the present embodiments herein in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Further, it will be apparent that modifications and variations are possible without departing from the scope of the present embodiments including, but not limited to, embodiments defined in the appended claims. More specifically, although some aspects of the present embodiments are identified herein as preferred or particularly advantageous, it is contemplated that the present embodiments is not necessarily limited to these aspects.

What is claimed is:

1. A process for capturing greenhouse gas emissions utilizing algae, the process comprising:

feeding a carbon dioxide feed stream, a recycle water stream, and light to a closed photobioreactor, thereby forming oxygen and the algae;

extracting the oxygen and at least a portion of the algae from the closed photobioreactor, the algae extracted as a wet biomass stream;

introducing the wet biomass stream to a dewatering unit along with an exhaust gas stream comprising carbon dioxide, thereby forming steam, a reduced temperature exhaust gas stream, and a dehydrated biomass product;

introducing at least a portion of the steam to a cooling unit, the cooling unit fluidly connected downstream from the dewatering unit, thereby condensing the steam and forming the recycle water stream;

introducing the reduced temperature exhaust gas stream to a treatment unit, the treatment unit comprising one or more absorption columns, oxidation columns, membrane separation columns, or combinations thereof, thereby forming the carbon dioxide feed stream;

conducting a machine learning algorithm, wherein the machine learning algorithm comprises clustering and classification portions and is executed by a controller, the controller comprising a plurality of actuators coupled to a plurality of control valves, the machine learning algorithm comprising:

monitoring a plurality of algae growth variables in the closed photobioreactor utilizing a plurality of sensors, the plurality of algae growth variables comprising a carbon dioxide content, a pH, a light intensity, a temperature, an oxygen content, and a nutrient content and the plurality of sensors comprising a gas chromatograph, a pH sensor, a photosensitive sensor, and a temperature sensor, concurrently monitoring a lifecycle of the algae via the oxygen content and the wet biomass stream extracted from the closed photobioreactor, determining sensitivities between the lifecycle of the algae and one or more of the plurality of the algae growth variables by varying the plurality of algae growth variables, and determining an optimized level of carbon dioxide content of the closed photobioreactor associated with an optimized and controlled lifecycle of the algae based on the sensitivities;

monitoring the carbon dioxide content of the closed photobioreactor; and varying the carbon dioxide content of the closed photobioreactor relative to the carbon dioxide content exceeding a predetermined tolerance from the optimized carbon dioxide content associated with the optimized and controlled lifecycle of the algae, via the controller, by varying one or more of:

a recycle rate of the carbon dioxide back to the treatment unit, an introduction rate of an external air source into the reduced temperature exhaust gas stream, the carbon dioxide feed stream, or both, or a recycle rate of oxygen into the carbon dioxide feed stream, further wherein the controller initiates one or more of the plurality of actuators to open and close one or more of the plurality of valves for altering the recycle rate of the carbon dioxide, the introduction rate, or the recycle rate of the oxygen.

2. The process of claim 1, wherein the exhaust gas stream originates from a combustion gas turbine.

3. The process of claim 1, further comprising:

monitoring a temperature of the recycle water stream concurrently with feeding of the recycle water stream to the closed photobioreactor; and varying the temperature of the recycle water stream relative to the temperature of the recycle water stream exceeding a predetermined tolerance from the optimized temperature of the recycle water stream associated with the optimized and controlled lifecycle of the algae, via the controller, by varying:

an introduction percentage of the steam into the cooling unit, a cooling capacity of the cooling unit, or both, further wherein the controller initiates one or more of the plurality of actuators to open and close one or more of the plurality of valves for altering the introduction percentage, the cooling capacity, or both.

4. The process of claim 1, further comprising supplementing the closed photobioreactor with a nutrient stream.

5. The process of claim 4, wherein the nutrient stream is mixed with the recycle water stream prior to being introduced to the closed photobioreactor.

6. The process of claim 2, wherein the dewatering unit comprises a heat recovery steam generator (HRSG).

* * * * *